United States Patent [19]

Metcalf et al.

[11] 4,190,586
[45] Feb. 26, 1980

[54] α-ACETYLENIC DERIVATIVES OF α-AMINO ACIDS

[75] Inventors: Brian W. Metcalf, Strasbourg; Michel Jung, Illkirch Graffenstaden, both of France

[73] Assignee: Merrell Toraude et Compagnie, Strasbourg, France

[21] Appl. No.: 947,940

[22] Filed: Oct. 2, 1978

Related U.S. Application Data

[62] Division of Ser. No. 812,267, Jul. 1, 1977, Pat. No. 4,133,964.

[51] Int. Cl.² ............... C07D 207/26; C07D 211/76
[52] U.S. Cl. ............... 260/326.45; 546/221; 546/243; 424/207; 424/274; 562/571
[58] Field of Search .............. 260/326.45; 546/221, 546/243

[56] References Cited

U.S. PATENT DOCUMENTS

| | | | |
|---|---|---|---|
| 3,255,112 | 6/1966 | Hoffman et al. | 546/243 |
| 3,959,356 | 5/1976 | Metcalf et al. | 546/243 |
| 4,041,041 | 8/1977 | Metcalf et al. | 546/243 |
| 4,147,873 | 4/1979 | Metcalf et al. | 546/243 |

Primary Examiner—Mary C. Lee
Attorney, Agent, or Firm—L. Ruth Hattan; Eugene O. Retter; George W. Rauchfuss, Jr.

[57] ABSTRACT

Novel acetylenic derivatives of α-amino acids of the following general structure:

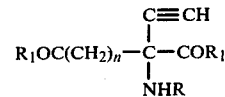

wherein n is an integer of from 1 to 3; R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or

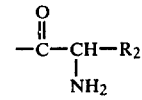

wherein $R_2$ is hydrogen, a straight or branched lower alkyl group of from 1 to 4 carbon atoms, benzyl or p-hydroxybenzyl; each $R_1$ is the same and is hydroxy, a straight or branched alkoxy group of from 1 to 8 carbon atoms, $-NR_3R_4$ wherein each of $R_3$ and $R_4$ is hydrogen or a lower alkyl group of from 1 to 4 carbon atoms and can be the same or different, or

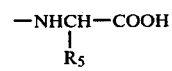

wherein $R_5$ is hydrogen, a straight or branched lower alkyl group of from 1 to 4 carbon atoms, benzyl or p-hydroxybenzyl; and the lactams thereof when n is 2 or 3; and pharmaceutically acceptable salts and individual optical isomers thereof.

4 Claims, No Drawings

α-ACETYLENIC DERIVATIVES OF α-AMINO ACIDS

This is a division of application Ser. No. 812,267, filed July 1, 1977, now U.S. Pat. No. 4,133,964.

FIELD OF INVENTION

This invention related to novel α-acetylenic α-amino acid derivatives which are useful pharmacological agents and useful as intermediates.

SUMMARY OF INVENTION

Compounds of the following general Formula I are novel derivatives useful as antibacterial agents, as central nervous system excitatory agents and as intermediates for the preparation of useful cephalosporin derivatives:

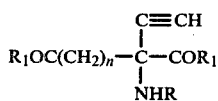

Formula I

In the above general Formula I n is an integer of from 1 to 3; each $R_1$ is the same and is hydroxy, a straight or branched alkoxy group of from 1 to 8 carbon atoms, $-NR_3R_4$ wherein each of $R_3$ and $R_4$ is hydrogen or a straight or branched lower alkyl group of from 1 to 4 carbon atoms and can be the same or different, or

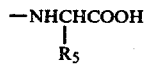

wherein $R_5$ is hydrogen, a straight or branched lower alkyl group of from 1 to 4 carbon atoms, benzyl or p-hydroxybenzyl; and R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or

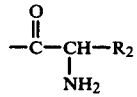

wherein $R_2$ is hydrogen, a straight or branched lower alkyl group of from 1 to 4 carbon atoms, benzyl or p-hydroxybenzyl. The lactams of the compounds of general Formula I wherein n is 2 or 3, and R is hydrogen are also included within the scope of the present invention and are represented by the following general Formula II:

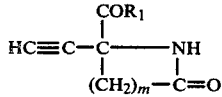

Formula II

In the above general Formula II m is the integer 2 or 3, and $R_1$ has the meaning defined in general Formula I.

Pharmaceutically acceptable salts of the compounds of general Formulas I and II and individual optical isomers of the compounds of general Formula I are included within the scope of the present invention.

DETAILED DESCRIPTION OF INVENTION

As used in general Formula I the term alkylcarbonyl is taken to mean the group

wherein the alkyl moiety has from 1 to 4 carbon atoms and is straight or branched, for example, methyl, ethyl, n-propyl, isopropyl, n-butyl, isobutyl and tert-butyl.

As used in general Formula I the term alkoxycarbonyl is taken to mean the group

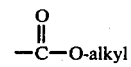

wherein the alkoxy moiety, that is, —O—alkyl, has from 1 to 4 carbon atoms and is straight or branched, for example, methoxy, ethoxy, n-propoxy, isopropoxy, n-butoxy, and tert-butoxy.

Illustrative examples of straight or branched alkyl groups having from 1 to 4 carbon atoms as used in general Formula I are methyl, ethyl, n-propyl, n-butyl, isopropyl and tert-butyl.

Illustrative examples of alkoxy groups having from 1 to 8 carbon atoms as used in general Formula I are methoxy, ethoxy, propoxy, butoxy, pentyloxy, and octyloxy.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids, such as, methane sulfonic, salicylic, maleic, malonic, tartaric, citric and ascorbic acids; and non-toxic salts formed with inorganic or organic bases such as those of alkali metals, for example, sodium, potassium and lithium, alkaline earth metals, for example, calcium and magnesium, light metals of Group III A, for example, aluminum, organic amines, such as, primary, secondary or tertiary amines, for example, cyclohexylamine, ethylamine, pyridine, methylaminoethanol, ethanolamine and piperazine. The salts are prepared by conventional means.

Preferred compounds of the present invention are those of general Formula I wherein each $R_1$ is hydroxy and within these preferred compounds those wherein R is hydrogen are more preferred. Compounds wherein n is the integer 2 are more preferred.

Illustrative examples of compounds of the present invention are the following:
2-acetylene-2-aminosuccinic acid,
2-acetyleneglutamic acid,
2-acetylene-2-aminoadipic acid,
2-acetylene-2-aminoadipic acid dimethyl ester,
2-acetylene-2-aminosuccinic acid dimethyl ester,
2-acetyleneglutamic acid dimethyl ester,
2-acetylene-2-aminoadipic acid dimethyl ester,
2-acetylene-2-aminosuccinic acid di-n-propyl ester,
2-acetyleneglutamic acid diethyl ester,
2-acetylene-2-aminoadipic acid di-isopentyl ester,
2-acetyleneglutamic acid di-tert-butyl ester,
2-acetylene-2-(1-oxoethyl)aminosuccinic acid dihexyl ester,
2-acetylene-2-(1-oxobutyl)aminoadipic acid dioctyl ester, 2-acetylene-2-(1-oxoethyl)aminoglutaric acid,
2-acetylene-2-(1-oxopropyl)aminoglutaric acid dimethyl ester,
2-acetylene-2-aminosuccinic acid diamide,
2-acetylene-2-aminoglutaric acid diamide,
2-acetylene-2-aminoadipic acid diamide,
2-acetylene-2-(1-oxopentyl)aminosuccinic acid diamide,
2-acetylene-2-(1-oxoethyl)aminoglutaric acid diamide,
2-acetylene-2-ethoxycarbonylaminoadipic acid diamide,
N,N'-dimethyl-2-acetylene-2-aminoglutaric acid diamide,
N,N,N',N'-tetraethyl-2-acetylene-2-aminoglutaric acid diamide,
N,N,N',N'-tetra-n-butyl-2-acetylene-2-(1-oxopropyl)aminoadipic acid diamide,
N,N'-dimethyl-2-acetylene-2-propoxycarbonylaminosuccinic acid diamide,
N,N'-(2-acetylene-2-amino-1,5-dioxo)pentylene bisaminoacetic acid,
N,N'-(2-acetylene-2-amino-1,4-dioxo)butylene bis-(α-methyl)aminoacetic acid, and
2-acetylene 2-(2-amino-1-oxoethyl)aminoglutaric acid.

The compounds of this invention wherein $R_1$ of the carboxy group proximal to the acetylene function is hydroxy are useful as intermediates for the preparation of cephalosporin derivatives of the following general Formula III which are useful as antibacterial agents.

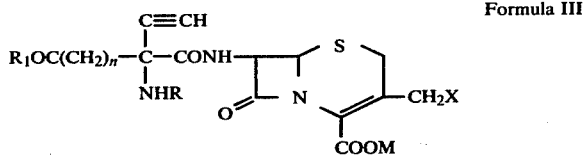

Formula III

In the above general Formula III n and R have the meanings defined in Formula I; M is hydrogen or a negative charge; and X is hydrogen or acetoxy.

The compounds of general Formula III and the pharmaceutically acceptable salts and individual optical isomers thereof are novel compounds useful as antibiotics and can be administered in a manner similar to that of many well known cephalosporin derivatives, for example, cephalexin, cephalothin, or cephaloglycine. The compounds of general Formula III and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formula III, salts and isomers thereof may be incorporated into creams or ointments.

Illustrative examples of bacteria against which the compounds of general Formula III and the pharmaceutically acceptable salts and individual optical isomers thereof are active are *Staphylococcus aureus, Salmonella schotmuehleri, Klebsiella pneumoniae, Diplococcus pneumoniae* and *Streptococcus pyogenes*.

Illustrative pharmaceutically acceptable non-toxic inorganic acid addition salts of the compouns of general Formula III are mineral acid addition salts, for example, hydrogen chloride, hydrogen bromide, sulfates, sulfamates, phosphate, and organic acid addition salts are, for example, maleate, acetate, citrate, oxalate, succinate, benzoate, tartrate, fumarate, malate and ascorbate. The salts can be formed by conventional means.

Illustrative examples of compounds of general Formula III are 7-[[2-acetylene-2-amino-4-carboxybutyryl]-amino]-3-acetyloxymethyl-8-oxo-5-thia-1-azabicyclo[4.2.0]-oct-2-ene-2-carboxylic acid and 7-[[2-acetylene-2-amino-4-methoxy-4-oxobutyrl]amino]-3-acetyloxymethyl-8-oxo-5-thia-1-azabicyclo[4.2.0]oct-2-ene-2-carboxylic acid.

The preparation of the compounds of general Formula III is described hereinbelow.

The compounds of general Formula I are useful as central nervous system excitatory agents, or central nervous system stimulants, and antibacterial agents, or microbicides. The compounds of general Formula I are also irreversible inhibitors of glutamic acid decarboxylase the enzyme which catalyzes in vivo the conversion of glutamic acid to γ-aminobutyric acid. As microbicides the compounds of general Formula I are useful in the control of microorganisms such as *E. coli* and other microorganisms which contain glutamic acid decarboxylase.

The utility of compounds of general Formula I as irreversible inhibitors of glutamic acid decarboxylase in vivo may be demonstrated as follows. A compound of general Formula I is administered to rats or mice as an aqueous solution or suspension orally or parenterally. At varying time intervals after administration of the test compound the animals are decapitated and their brains homogenized in phosphate buffer. Glutamic acid decarboxylase activity in these homogenates is measured as described by M. J. Jung et al., J. Neurochem. 28, 717–723 (1977).

As irreversible inhibitors of glutamic acid decarboxylase the compounds of general Formula I provide a means of studying the physiological role of γ-aminobutyric acid.

As pharmacologically useful agents the compounds can be administered in various manners to the patient being treated to achieve the desired effect. The compounds can be administered alone or in the form of a pharmaceutical preparation orally, parenterally, for example, intravenously, or topically. The amount of compound administered will vary over a wide range and can be any effective amount. Depending on the patient to be treated, the conditon being treated and the mode of administration, the effective amount of compound administered will vary from about 0.1 mg/kg to 250 mg/kg of body weight of the patient per unit dose and preferably will be about 1 mg/kg to about 50 mg/kg of body weight of patient per unit dose. For example, a typical unit dosage form may be a tablet containing from 10 to 300 mg of a compound of Formula I which may be administered to the patient being treated 1 to 4 times daily to achieve the desired effect.

As used herein the term patient is taken to mean warm blooded animals such as mammals, for example, cats, dogs, rats, mice, guinea pigs, sheep, horses, bovine cows, and humans.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers of synthetic silicones, for example, Silastic, silicone rubber manufactured by the Dow-Corning Corporation.

The compounds of general Formula I wherein each $R_1$ is hydroxy are prepared by treating a lower alkyl 2-tri(lower)alkylsilylacetylene-N-carbethoxyglycinate with a strong base an alkylating the thus formed dianion with an alkylating reagent selected from methyl acrylate, methyl bromoacetate and spiro-(2,5)-5,7-dioxa-6,6-dimethyloctan-4,8-dione in a suitable solvent in the presence of a complexing agent such as, N,N,N',N'-tetramethylethylenediamine or hexamethylphosphortriamide followed by acid hydrolysis. The lower alkyl groups are straight or branched having from 1 to 4 carbon atoms, for example methyl, ethyl, propyl or tert-butyl.

The alkylating reaction may be carried out in an aprotic solvent, for example, benzene, toluene, ethers, tetrahydrofuran, dimethylsulfoxide, dimethylformamide, dimethylacetamide, or hexamethylphosphoramide. The reaction temperature varies from about $-120°$ C. to about $25°$ C., a preferred reaction temperature being about $-70°$ C. The reaction time varies from about ½ hour to about 24 hours.

The hydrolysis step can be achieved by treatment with aqueous acid, for example, hydrochloric acid. The alkylating reagents are commercially available or can be prepared by procedures known in the art.

Suitable strong bases which may be employed in the above reaction are, for example, alkyl lithium, for example, butyl lithium or phenyl lithium, lithium di-alkylamide, for example, lithium diisopropylamide, lithium amide, tertiary potassium butylate or sodium amide.

The reactant lower alkyl 2-tri-(lower)alkylsilylacetylene-N-carbethoxyglycinate is prepared by reacting one equivalent of a lower alkyl N-carbethoxy-2-chloroglycinate with one equivalent of 2-tri-(lower)alkylsilylacetylene in the presence of aluminum chloride. Lower alkyl N-carbethoxy-2-chloroglycinates are prepared by the general procedure described by U. Zoller and B. Ben-Ishai, Tetrahedron, 31, 863 (1975) by substituting ethyl carbamate for benzyl carbamate.

The compounds of this invention wherein each $R_1$ is a straight or branched alkoxy group of from 1 to 8 carbon atoms are prepared from the corresponding derivatives wherein $R_1$ is hydroxy by reaction with an alcohol of the formula $R_6OH$, wherein $R_6$ is a straight or branched alkyl group of from 1 to 8 carbon atoms, saturated with HCl gas at about $25°$ C. for from about 12 to 36 hours.

The compounds of general Formula I wherein each $R_1$ is a straight or branched alkoxy group of from 1 to 8 carbon atoms may also be prepared by converting the corresponding compound wherein each $R_1$ is hydroxy to the acid halide by, for example, treatment with thionyl chloride, followed by alcoholysis with an alcohol of the formula $R_6OH$ as defined above by procedures generally known in the art.

The compounds of Formula I wherein each $R_1$ is $NR_3R_4$ and each of $R_3$ and $R_4$ is hydrogen or a straight or branched lower alkyl group of 1 to 4 carbon atoms are prepared by an acylation reaction of an acid halide, for example, an acid chloride, of the corresponding compound wherein each $R_1$ is hydroxy and R has the meaning defined in Formula I with the proviso that any free amino group is suitably protected with protecting groups, such as, carbobenzyloxy or tert-butoxycarbonyl, with an excess of an appropriate amine which may be represented as $HNR_3R_4$. The reaction is carried out in methylene chloride, chloroform, dimethylformamide, ethers, such as, tetrahydrofuran or dioxane, or benzene at about $25°$ C. for about 1 to 4 hours. Suitable amines are ammonia, or a compound which is a potential source of ammonia, for example, hexamethylenetetramine; primary amines, for example methylamine, ethylamine or n-propylamine; and secondary amines, for example, dimethylamine, diethylamine or di-n-butylamine. Following the acylation reaction the protecting groups are removed by treatment with acid, for example, trifluoroacetic acid or hydrogen bromide in dioxane.

The compounds of general Formula I wherein each $R_1$ is

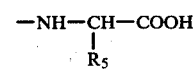

are prepared by reacting the corresponding derivative wherein each $R_1$ is hydroxy or a functional derivative thereof such as an acid anhydride and R has the meaning defined in Formula I with the proviso that any free amino group is protected with a suitable blocking group, such as benzyloxycarbonyl, tert-butoxycarbonyl with a compound of the formula

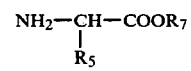

wherein $R_5$ has the meaning defined in general Formula I and $R_7$ is a lower alkyl group, for example, methyl or ethyl in an ether solution, such as, tetrahydrofuran or dioxane at about $0°$ to $50°$ C. for 1 to 24 hours followed by acid hydrolysis with, for example, trifluoroacetic acid or hydrogen bromide in dioxane for about 1 to 20 hours to remove the protecting group, with the proviso that when the amine protected free acid is employed the reaction is carried out using a dehydrating agent such as dicyclohexylcarbodiimide.

The compounds of general Formula I wherein R is alkylcarbonyl wherein the alkyl moiety is straight or branched and has from 1 to 4 carbon atoms are prepared by treating the corresponding derivatives wherein R is hydrogen and $R_1$ is hydroxy with an acid halide of the formula

wherein halo is a halogen atom, for example, chlorine or bromine and $R_8$ is a straight or branched alkyl group having from 1 to 4 carbon atoms or an appropriate acid anhydride in water in the presence of a base such as sodium hydroxide or sodium borate at a temperature of from 0° to about 25° C. for from ½ hour to about 6 hours. These compounds may also be prepared from the ester derivative, that is, compounds of general Formula I wherein R is hydrogen and each $R_1$ is an alkoxy group of from 1 to 8 carbon atoms by treatment with the acid halide,

described above, or an appropriate acid anhydride in water, methylene chloride, chloroform or dimethyl acetamide in the presence of a base such as sodium hydroxide, potassium hydroxide or excess triethylamine at a temperature of from 0° to about 25° C. for from ½ hour to about 24 hours.

The compounds of general Formula I wherein R is alkoxycarbonyl wherein the alkoxy moiety is straight or branched and has from 1 to 4 carbon atoms are prepared by treating the corresponding derivative wherein R is hydrogen and each $R_1$ is hydroxy with a halo alkylformate of the formula

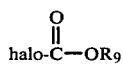

wherein halo is a halogen atom such as chlorine or bromine and $R_9$ is a straight or branched alkyl group having from 1 to 4 carbon atoms in water in the presence of a base such as sodium hydroxide or sodium borate at a temperature of from 0° to about 25° C. for from ½ hour to about 6 hours.

The compounds of general Formula I wherein R is

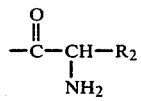

wherein $R_2$ is hydrogen, a straight or branched lower alkyl group of from 1 to 4 carbon atoms, benzyl or p-hydroxybenzyl are prepared by treating the corresponding derivative wherein R is hydrogen and $R_1$ is a straight or branched alkoxy group of from 1 to 8 carbon atoms with an acid of the formula

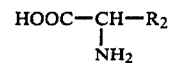

or an anhydride thereof wherein $R_2$ has the meaning defined above and the amino group is protected with a suitable blocking group, such as, benzyloxycarbonyl or tert-butoxycarbonyl in an ether, such as, tetrahydrofuran or dioxane, methylene chloride or chloroform and in the presence of a dehydrating agent, such as, dicyclohexylcarbodiimide when the free acid is employed, at a temperature of from 0° to about 35° C. for 1 to about 12 hours followed by acid hydrolysis with, for example, trifluoroacetic acid or hydrogen bromide in dioxane and base hydrolysis to remove the protecting groups.

The lactams of this invention, that is, compounds of general Formula II, are prepared by heating a diester derivative of the corresponding amino acid of the structure

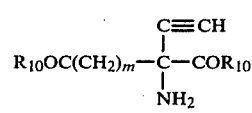

wherein m is the integer 2 or 3, and $R_{10}$ is a straight or branched alkoxy group of from 1 to 8 carbon atoms in a lower alcohol, such as ethanol or 2-methoxyethanol for 1 to about 24 hours at a temperature of from about 80° to about 120° C.

The individual optical isomers of the compounds of general Formula I wherein R is hydrogen and $R_1$ is hydroxy may be separated by using a (+) or (−) binaphthylphosphoric acid salt by the method described by R. Viterbo et al., in Tetrahedron Letters 48, 4617–4620 (1971) and in U.S. Pat. No. 3,848,030. Other resolving agents such as (+) comphor-10-sulfonic acid may also be employed. The individual optical isomers wherein R is other than H and $R_1$ is other than OH may be obtained as described herein for the racemic mixture only starting with the resolved amino acid.

The compound of general Formula I wherein n is 2 and R is hydrogen, that is, 2-acetyleneglutamic acid may also be prepared by treating a suitably protected propargylamine derivative with a strong base to form a protected propargylamine carbanion intermediate which is reacted with an alkylating reagent of the formula

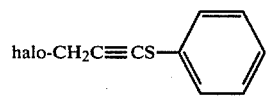

wherein halo is a halogen atom, for example, chlorine or bromine, treating the thus formed alkylated protected propargylamine derivative with a strong base to form an alkylated carbanion, acylating said second carbanion with methyl chloroformate and subsequently removing the protecting groups by acid or base hydrolysis as represented by the following reaction scheme:

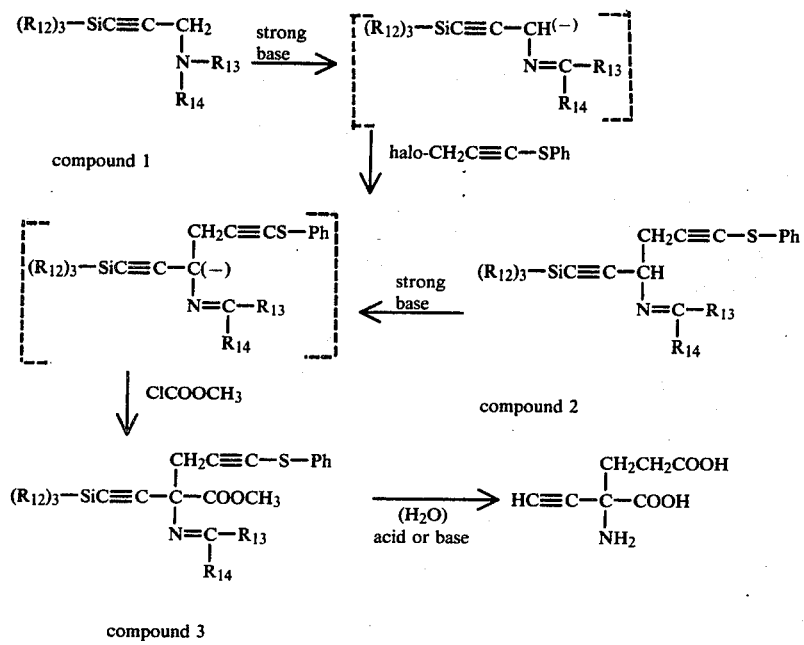

compound 1 compound 2 compound 3

In the above reaction scheme Ph means phenyl; $R_{12}$ is a straight or branched lower alkyl group having from 1 to 4 carbon atoms, such as, methyl, ethyl, n-propyl, isopropyl, n-butyl and tert-butyl; $R_{13}$ is phenyl, tert-butyl, tri-ethylmethyl, 1-adamantanyl or 2-furyl; $R_{14}$ is hydrogen, methoxy or ethoxy with the proviso that when $R_{13}$ is 1adamantanyl or 2-furyl, $R_{14}$ is not hydrogen.

Suitable strong bases which may be employed in the above reaction to form each carbanion are those that will abstract a proton from the carbon atom adjacent to the acetylene moiety, such as, alkyl lithium, for example, butyl lithium or phenyl lithium, lithium di-alkyla-mide, for example, lithium diisopropylamide, lithium amide, tertiary potassium butylate or sodium amide.

The alkylating reaction and the acylating reaction may be carried out in an aprotic solvent, for example, benzene, toluene, ethers, tetrahydrofuran, dimethylsulf-oxide or dimethylformamide. For each reaction the temperature varies from $-120°$ C. to about $25°$ C., a preferred reaction temperature being about $-70°$ C., and the reaction time varies from about ½ hour to about 24 hours.

Removal of the protecting groups, as represented in the reaction scheme in the step going from compounds 3 to compounds of Formula IV, is achieved by treatment with aqueous acid, for example, hydrochloric acid or toluene sulfonic acid, or aqueous base, for example, sodium hydroxide or potassium hydroxide. Optionally hydrazine or phenylhydrazine may be employed in removing the protecting groups followed by treatment with aqueous acid or base.

The propargylamine derivatives, that is, compounds 1, wherein $R_{14}$ is hydrogen are prepared by the addition of protecting groups on the acetylene function and the nitrogen function of propargylamine. Protection of the nitrogen function of the propargylamine is accomplished by forming in a known manner a Schiff's base with a nonenolizable carbonyl bearing compound selected from benzaldehyde, 2,2-dimethylpropanal and 2,2-diethylbutanal. Protection of the acetylenic function is accomplished by reacting the above-described Schiff's base with a trialkylsilylchloride wherein the alkyl moiety has from 1 to 4 carbon atoms and is straight or branched, for example, trimethylsilylchloride or triethylsilylchloride forming in a known manner the corresponding trialkylsilyl derivative.

The propargylamine derivatives, compounds 1, wherein $R_{14}$ is methoxy or ethoxy are prepared by reacting propargylamine wherein the acetylene function is protected by a trialkylsilyl group, wherein the moiety has from 1 to 4 carbon atoms, with benzoyl chloride, pivalic acid chloride, 2,2-diethylbutyric acid chloride, 2-furoic acid chloride or 1-adamantane carboxylic acid chloride at $0°$ C. in diethyl ether, dioxane, tetrahydrofuran, chloroform, methylenechloride, dimethylformamide, dimethylacetamide, or chlorobenzene in the presence of an organic base such as triethylamine or pyridine after which the reaction mixture is allowed to warm to about $25°$ C. for one hour. The resulting amide derivative is combined with an alkylating reagent, such as, methylfluorosulfonate, dimethylsulfate, methyliodide, methyl p-toluenesulfonate or trimethyloxonium hexafluorophosphate when $R_{14}$ is methoxy and triethyloxonium tetrafluoroborate when $R_{14}$ is ethoxy, at about $25°$ C. in a chlorinated hydrocarbon solvent such as methylene chloride, chlorobenzene or chloroform, and the reaction mixture is refluxed for about 12 to 20 hours. The mixture is then cooled to about $25°$ C. and an organic base such as triethylamine or pyridine is added, after which the solution is extracted with brine and the product isolated.

The protected propargylamine starting material is obtained by treating a 3-trialkylsilylprop-2-ynyl-1-iminobenzyl derivative, that is, compounds 1 wherein $R_{14}$ is hydrogen and $R_{13}$ is phenyl with hydrazine or phenylhydrazine at about $25°$ C. for about ½ hour after which the mixture is diluted with, for example, petroleum ether, benzene or toluene and the propargylamine derivative isolated. Alternatively treatment with 0.5 to 1 N HCl gives the hydrochloride. The 3-trialkylsilylprop-2-ynyl-1-iminobenzyl derivative is obtained from propargylamine by forming in a known manner a Schiff's base with benzaldehyde and reacting said Schiff's base with a base such as an alkyl Grignard or alkyl lithium followed with an appropriate trialkylsilylchloride, for example, trimethylsilylchloride in a known manner (E. J. Corey and H. A. Kirst, Tetrahedron Letters 1968, 5041).

The compound of general Formula I wherein n is 2 and R is hydrogen may also be prepared by treating 2-acetylene-2-amino-4-(1,3-dioxolan-2-yl)butyric acid in HCl-lower alkanol, such as methanol with an organic amine such as triethylamine and an acyl halide, such as, acetyl chloride, hydrolyzing with acid the thus formed ester amide acetal to the aldehyde, oxidizing the aldehyde followed by acid hydrolysis.

As set forth hereinabove compounds of general Formula I are useful as intermediates for the preparation of useful cephalosporin derivatives as described by general Formula III. The compounds of general Formula III wherein R is hydrogen and R₁ is hydroxy are prepared by coupling 7-aminocephalosporanic acid or a derivative thereof having the formula

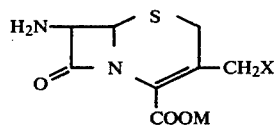

Formula V wherein X and M have the meanings defined in general Formula III with an acid of the formula

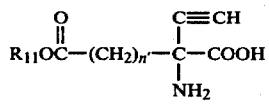

Formula VI or a functional derivative thereof, such as, the acid chloride or an acid anhydride and in the presence of a dehydrating agent such as dicyclohexyl carbodiimide when the acid is employed wherein R₁₁ is tert-butyl or benzyl; n' is an integer of from 1 to 3; and the amino group is protected by suitable blocking groups, for example, benzyloxycarbonyl, followed by acid and base hydrolysis to remove the protecting groups.

The coupling reaction is generally carried out in a solvent, such as, ethyl acetate, dioxane, chloroform, or tetrahydrofuran in the presence of a base, such as, alkaline bicarbonate. The temperature of the reaction may vary from about −10° C. to 100° C., and the reaction time may vary from about ½ hour to 10 hours. The cephalosporin products are isolated by conventional procedures.

The acids of Formula VI are prepared by procedures generally known in the art. for example, the compounds of Formula VI wherein R₁₁ is tert-butyl may be prepared by selective hydrolysis of the corresponding dicarboxylic acid ester derivative by aqueous copper sulfate with isolation of the monoester by the general procedure described by R. L. Prestidge, et al., J. Org. Chem. 40, 3287 (1975).

The compounds of general Formula III wherein R is other than hydrogen and R₁ is other than hydroxy are prepared from the corresponding derivatives wherein R is hydrogen and R₁ is hydroxy by the general procedures set forth hereinabove for the compounds of general Formula I wherein R is other than hydrogen and R₁ is hydroxy. To prepare compounds of general Formula III wherein M is hydrogen and R₁ is other than hydroxy protection of the cephalosporin acid group by, for example, conversion to the tert-butyl ester prior to coupling may be desirable.

The following examples further illustrate the invention.

EXAMPLE 1

Methyl 2-trimethylsilylacetylene-N-carbethoxyglycinate

To 19.5 g (0.1 M) of methyl N-carbethoxy-2-chloroglycinate and 17.0 g (0.1 M) of di-trimethylsilyl acetylene in 200 ml of methylene chloride at 0° C. is added 13.5 g (0.1 M) of aluminum chloride and the reaction mixture was allowed to warm to 25° C. After 24 hours at 25° C. water was carefully added to the mixture which was then extracted with methylene chloride. The combined organic solutions were dried over magnesium sulfate, concentrated and distilled with the b.p. 110°/0.15 mm fraction collected to give methyl 2-trimethylsilylacetylene-N-carbethoxyglycinate.

EXAMPLE 2

2-Acetyleneglutamic Acid

To a solution of lithium diisopropylamide, prepared from 1.01 g (0.01 mole) of diisopropylamine and 5 ml of a 2.0 M solution (0.01 mole) of n-butyllithium, and 1.16 g (0.01 mole) of N,N,N',N'-tetramethylethylenediamine in 30 ml of tetrahydrofuran at −70° C. is added 1.28 g (0.005 mole) of methyl 2-trimethylsilylacetylene-N-carbethoxyglycinate. After 30 minutes at −70° C. 430 mg (0.005 mole) of methyl acrylate in 5 ml of tetrahydrofuran is added and the solution is maintained at −70° C. for 30 minutes. The reaction mixture is then neutralized using aqueous ammonium chloride and extracted with ether. The ether extract is washed with aqueous ammonium chloride, dried over magnesium sulfate and concentrated. The residue is distilled with the b.p. 140°/0.05 mm fraction collected to give dimethyl N-carbethoxy-2-trimethylsilylacetyleneglutamate which is heated at reflux with 5 ml of 6 N HCl for 24 hours then evaporated to dryness. The residue is dissolved in a minimum quantity of ethanol to which is added 150 mg of aniline, and the mixture is maintained at 0° C. for 16 hours. The resulting precipitate is filtered to give 2-acetyleneglutamic acid.

EXAMPLE 3

2-Acetylene-2-aminoadipic Acid

To a solution of lithium diisopropylamide, prepared from 1.01 g (0.01 mole) of diisopropylamine and 5 ml of a 2.0 M solution (0.01 mole) of n-butyllithium and 1.16 g (0.01 mole) of N,N,N',N'-tetramethylethylenediamine in 30 ml of tetrahydrofuran at −70° C. is added 1.28 g (0.005 mole) of methyl 2-trimethylsilylacetylene-N-carbethoxyglycinate. After 30 minutes at −70° C. 850 g (0.005 mole) of spiro(2,5)-5,7-dioxa-6,6-dimethyloctan-4,8-dione is added, and the solution is maintained at −70° C. for 30 minutes. The reaction mixture is then neutralized using aqueous ammonium chloride, dried over magnesium sulfate and concentrated. The residue is distilled with the b.p. 140°/0.05 mm fraction isolated which fraction is heated at reflux with 5 ml of 6 N HCl for 24 hours then evaporated to dryness. The residue is dissolved in a minimum amount of ethanol to which is added 150 mg of aniline, and the mixture is maintained at 0° C. for 16 hours. The resulting precipitate is filtered to give 2-acetylene-2-aminoadipic acid.

EXAMPLE 4

2-Acetylene-2-aminosuccinic Acid

To a solution of lithium diisopropylamide prepared from 1.01 g (0.01 mole) of diisopropylamine and 5 ml of a of a 2.0 M solution (0.01 mole) of n-butyllithium, and 1.16 g (0.01 mole) of N,N,N',N'-tetramethylethylenediamine in 30 ml of tetrahydrofuran at −70° C. is added 1.28 g (0.005 mole) of methyl 2-trimethylsilylacetylene-N-carbethoxyglycinate. After 30 minutes at −70° C. 760 mg (0.005 mole) of methyl bromoacetate in 5 ml of tetrahydrofuran is added. The solution is maintained at −70° C. for 30 minutes, neutralized using aqueous ammonium chloride and extracted with ether. The ether extract is washed with aqueous ammonium chloride, dried over magnesium sulfate and concentrated. The concentrate is distilled with the b.p. 135°/0.05 mm fraction isolated which fraction is heated at reflux for 24 hours with 5 ml of 6 N HCl then evaporated to dryness. The residue is dissolved in a minimum of ethanol to which is added 150 mg of aniline, and the mixture is maintained at 0° C. for 16 hours. The resulting precipitate is filtered to give 2-acetylene-2-aminosuccinic acid.

EXAMPLE 5

7-[[2-Acetylene-2-amino-4-carboxybutyryl]amino]-3-acetyloxymethyl-8-oxo-5-thia-1-azabicyclo[4.2.0]oct-2-ene-2-carboxylic Acid A mixture of 1 gram of 3-acetyloxy-7-amino-8-oxo-5-thia-1-azabicyclo[4.2.0]oct-2-ene-2-carboxylic acid and 1 g of 2-acetylene-4-benzyloxycarbonylglutamic acid chloride wherein the free amino group is protected with tert-butoxycarbonyl in 50 ml of ethyl acetate is refluxed for 2 hours after which the solvent is removed leaving a residue which is treated with mild acid and chromatographed on silica gel using benzene-acetone as the eluant to give 7-[[2-acetylene-2-amino-4-carboxybutyryl]amino]-3-acetyloxymethyl-8-oxo-5-thia-1-azabicyclo[4.2.0]oct-2-ene-2-carboxylic acid.

The following examples are illustrative of pharmaceutical preparations of compounds of general Formula I.

EXAMPLE 6

An illustrative composition for hard gelatin capsules is as follows:
(a) 2-acetyleneglutamic acid—10 mg
(b) talc—5 mg
(c) lactose—100 mg The formulation is prepared by passing the dry powders of (a) and (b) through a fine mesh screen and mixing them well. The powder is then filled into hard gelatin capsules at a net fill of 115 mg per capsule.

EXAMPLE 7

An illustrative composition for tablets is as follows:
(a) 2-acetyleneglutamic acid—5 mg
(b) starch—43 mg
(c) lactose—60 mg
(d) magnesium stearate—2 mg The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 8

An illustrative composition for an injectable suspension is the following 1 ml ampul for an intramuscular injection.

|  | Weight per cent |
|---|---|
| (a) 2-acetylene-2-aminosuccinic acid | 1.0 |
| (b) polyvinylpyrrolidone | 0.5 |
| (c) lecithin | 0.25 |
| (d) water for injection to make | 100.0 |

The materials (a)–(d) are mixed, homogenized, and filled into 1 ml ampuls which are sealed and autoclaved 20 minutes at 121° C. Each ampul contains 10 mg per ml of novel compound (a).

EXAMPLE 9

Dimethyl-2-acetylene-glutamate

2-Acetylene glutamic acid (500 mg, 2.9 mM) is added to methanol (40 ml) which is saturated with dry hydrogen chloride. The solution is heated at reflux for 12 hours, then the solvent evaporated to afford dimethyl-2-acetyleneglutamate.

EXAMPLE 10

N-Acetyl-2-acetylene glutamic Acid

To a solution of 2-acetylene glutamic acid (350 mg, 2 mM) in 5 ml of 1 N sodium hydroxide at 0° C. are added simultaneously from 2 syringes acetyl chloride (160 mg) diluted in dioxane (1 ml) and 2 ml of 1 N sodium hydroxide. After 30 minutes at 0° the solution is acidified by the addition of 6 N hydrochloric acid, then extracted well with dichloromethane. The organic phase is dried and concentrated to afford N-acetyl-2-acetylene glutamic acid.

In a similar manner, but with acetyl chloride replaced by ethyl chloroformate (220 mg), N-ethoxycarbonyl-2-glutamic acid is obtained.

EXAMPLE 11

N,N'-Dipropyl-2-acetylenegultamic Acid bis-carboxamide HBr

To a solution of 2-acetylene glutamic acid (350 mg, 2mM) in 5 ml of 1 N sodium hydroxide at 0° are added simultaneously from two syringes benzyl chloroformate (340 mg, 2 mM) in dioxane (1 ml) and 2 ml of 1 N sodium hydroxide. After 30 minutes at 0° the solution is acidified by the addition of 6 N hydrochloric acid, then extracted well with dichloromethane. The organic phase is dried and concentrated to afford N-(benzyloxycarbonyl)-2-ethynyl glutamic acid. This was dissolved in dichloromethane (15 ml) and treated with thionyl chloride (238 mg) at 25° for one hour. Propylamine (500 mg) is then added and the solution stirred at 25° for one hour, then washed with water, dried and concentrated. The residue is treated with 6 ml of a solution of dioxane containing hydrogen bromide (40% w/w) and allowed to stand for 30 minutes at 25°. Ether (50 ml) is then added and the resulting precipitate collected to afford N,N'-dipropyl-2-acetyleneglutamic acid bis-carboxamide HBr.

EXAMPLE 12

5-Acetylene-5-amino-2,10-dimethyl-4,8-dioxo-3,9-diazaundecanedioic Acid

To 2-acetylene-2-(benzyloxycarbonyl)aminoglutaric acid (305 mg, 1 mM) in methylene chloride (15 ml) is added triethylamine (205 mg, 2 mM) followed by ethyl chloroformate (218 mg, 2 mM). The solution is stirred for one hour at 25°, then alanine methyl ester (206 mg, 2 mM) in methylene chloride (5 ml) is added. This solution is kept overnight at 25° C., washed with water, dried and evaporated to dryness. The residue is treated with 5 ml of a 40% (w/w) solution of hydrogen bromide in dioxane at 25° for 30 minutes. Ether (50 ml) is then added and the precipitate collected. This is then treated with 20 ml of a 1 N sodium hydroxide solution overnight at 25°, the pH adjusted to 6.5, and applied to an Amberlite 120 H+ resin. Elution with 2 N ammonium hydroxide afforded 5-acetylene-5-amino-2,10-dimethyl-4,8-dioxo-3,9-diazaundecanedioic acid.

EXAMPLE 13

5-Acetylene-5-methoxycarbonyl-2-pyrrolidone

Dimethyl-2-acetyleneglutamate hydrochloride (570 mg, 2mM) is treated with saturated aqueous sodium carbonate (20 ml) and the resulting mixture extracted with dichloromethane. The organic phase is dried and concentrated to afford the free base which is dissolved in 2-methoxyethanol (20 ml) and heated under reflux for 2 hours. The solvent is then removed in vacuo to afford 5-acetylene-5-methoxycarbonyl-2-pyrrolidone.

5-Acetylene-5-carboxy-2-pyrrolidone is prepared by treatment of the lactam ester (360 mg, 2 mM) with aqueous sodium hydroxide (10 ml of a 1 N solution) at room temperature for 3 hours. The solution is then acidified (2 N hydrochloric acid) and extracted exhaustively with chloroform. The organic phase is dried and evaporated to afford 5-acetylene-5-carboxy-2-pyrrolidone.

EXAMPLE 14

2-Acetylene-N-(2-aminopropylcarbonyl) glutamic Acid

Dimethyl-2-acetylene glutamate (200 mg, 1 mM) in methylene chloride (4 ml) is treated with N-carbobenzoxy alanine (200 mg, 1 mM) and N,N'-dicyclohexylcarbodimide (206 mg, 1 mM) overnight at 25° C. The mixture is then cooled to 0° and the precipitated dicyclohexyl urea filtered off. The filtrate is diluted with methylene chloride, washed with water, bicarbonate, dilute hydrochloric acid, then dried and concentrated. The residue is treated with ethanol (5 ml) and 5 ml of a 40% (w/w) solution of hydrogen bromide in dioxane for 30 minutes at 25°. Ether (50 ml) is then added and the resulting precipitate collected which is treated with 1 N sodium hydroxide (15 ml) overnight at 25°. The pH of the solution is adjusted to neutral and the product isolated from an Amberlite 120 H+ resin by elution with 2 M ammonium hydroxide affording 2-acetylene-N-(2-aminopropylcarbonyl) glutamic acid.

EXAMPLE 15

1-Phenylsulfenylpropargyl Chloride

A solution of propargylic chloride (10 g, 135 mM) in tetrahydrofuran (200 ml) at −70° C. is treated with n-BuLi (67 ml of a 2.0 M solution, 135 mM). Phenylsulfenyl chloride (15.1 g, 135 mM) in tetrahydrofuran (20 ml) is added. After 15 minutes the solution is treated with aqueous ammonium chloride and the product isolated by ether extraction. The sulfide is purified by chromatography on silica gel to give 1-phenylsulfenylpropargyl chloride as an oil (9.0 g).

EXAMPLE 16

2-Acetyleneglutamic Acid 24.5 g (0.1 mole) of methyl N-(3-trimethylsilylprop-2-ynyl)benzene carboximidate in 50 ml of tetrahydrofuran is added to lithium diisopropylamide, prepared from 1.01 g (0.01 mole) of diisopropylamide and 5 ml of a 2.0 M solution (0.01 mole) of n-butyllithium, at −70° C. After 15 minutes 18.2 g (0.1 mole) of 1-phenylsulfenylpropargyl chloride is added. Thirty minutes later 50 ml of a 2 M solution of n-butyllithium is added at −70° C. followed by the addition of 9.4 g (0.1 mole) of methyl chloroformate. The reaction mixture is treated 10 minutes later with brine then extracted with ether. The ether extract is dried and concentrated to dryness. The resulting residue is heated with 100 ml of 3 N HCl for 12 hours. On cooling the solution is washed well with methylene chloride then evaporated to dryness. The residue is taken up in water and the pH adjusted to 6. The solution is applied to a column of Amberlite 120 H+ and eluted with 2 M ammonium hydroxide to afford 2-acetyleneglutamic acid which is recrystallized from ethanol/water.

EXAMPLE 17

2-Acetylene-2-amino-4-(1,3-dioxolan-2-yl)butyric Acid

A solution of 9.8 g (0.046 mole) of 3-trimethylsilylprop-2-ynyl-1-iminobenzyl in 200 ml of tetrahydrofuran is treated at −78° C. with 24 ml of a 1.95 M solution of n-butyllithium afterwhich 9.0 g (0.043 mole) of 2-(2-bromoethyl)-1,3-dioxolane is added. The mixture is maintained at −30° C. for 3 hours then water was added and 1-trimethylsilyl-3-iminobenzyl-6-ethylenedioxyhex-1-yne is isolated by ether extraction.

A solution of 6.9 g (0.02 mole) of the above-obtained hexyne derivative in 100 ml of tetrahydrofuran at −78° C. is treated with 10 ml of a 2 M solution of n-butyllithium after which 1.9 g (0.01 mole) of methyl chloroformate in 5 ml of tetrahydrofuran is added. After 15 minutes the reaction mixture is quenched with brine to give crude 1-trimethylsilyl-3-carbomethoxy-3-iminobenzyl-6-ethylenedioxyhex-1-yne isolated by ether extraction.

A solution of 7.0 g of the crude 1-trimethylsilyl-3-carbomethoxy-3-iminobenzyl-6-ethylenedioxyhex-1-yne in 100 ml of petroleum ether (B.P. 30°–60°) is treated with 2.1 g (0.02 mole) of phenylhydrazine for 2 hours at 25° C. The precipitate is filtered off, the petroleum ether is evaporated and the residue, taken up in 50 ml of ethanol and 50 ml of water, is treated with 3.3 g (0.06 mole) of potassium hydroxide for 1 hour at 25° C. The ethanol is evaporated, and the aqueous residue is washed well with methylene chloride then carefully neutralized with 1 N HCl. The resulting precipitate is collected and recrystallized from ethanol to give 2-acetylene-2-amino-4-(1,3-dioxolan-2-yl)butyric acid.

EXAMPLE 18

Methyl 2-acetylene-2-(1'-oxoethylamino)-5-oxopentanoate

2-Acetylene-2-amino-4-(1,3-dioxolan-2-yl)-butyric acid (400 g, 2 mM) is added to methanol (20 ml) which had been saturated with dry hydrogen chloride. The solution is then heated under reflux overnight, then the solvent evaporated. The residue is treated with aqueous sodium bicarbonate and extracted with methylene chloride. The methylene chloride solution is washed well with water, dried and evaporated. The residue, in methylene chloride (10 ml), is treated with triethylamine (200 mg, 2 mM) followed by acetyl chloride (160 mg, 2 mM). After 1 hour at 25° C., the solution is diluted with methylene chloride and washed with sodium bicarbonate solution, then with water. The solution is dried and concentrated to afford methyl-2-acetylene-2-(1'-oxoethyl)amino-5-diethoxyacetal pentanoate which is dissolved in ethanol (5 ml), after which 0.5 N hydrochloric acid (5 ml) is added, and the solution then stirred at 25° C. for 3 hours, then extracted well with ether. The ether solution is dried and concentrated to afford methyl 2-acetylene-2-(1'-oxoethylamino)-5-oxopentanoate.

EXAMPLE 19

2-Acetyleneglutamic Acid

To 1 g of methyl-2-acetylene-2-(1-oxoethylamino)-5-oxopentanoate in 7 ml of acetone is added dropwise Jones reagent until a brown color persists after which the mixture is stirred at 25° C. for 2 hours then poured into water and extracted well with ether. The ether solution is dried and concentrated leaving a residue which is heated with 20 ml of 6 N HCl for 6 hours after which the solvent is evaporated leaving a residue which is dissolved in the minimum volume of ethanol. The ethanol solution is treated with 410 mg of aniline and cooled to 0° C. The resulting precipitate is collected affording 2-acetyleneglutamic acid.

We claim:

1. A compound of the formula

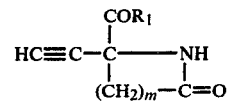

wherein m is the integer 2 or 3, and $R_1$ is hydroxy, a straight or branched alkoxy group of from 1 to 8 carbon atoms, $-NR_3R_4$ wherein each of $R_3$ and $R_4$ is hydrogen or a lower alkyl group of from 1 to 4 carbon atoms and can be the same or different, or

wherein $R_5$ is hydrogen, a straight or branched lower alkyl group of from 1 to 4 carbon atoms, benzyl or p-hydroxybenzyl; and pharmaceutically acceptable salts and individual optical isomers thereof.

2. A compound of claim 1 wherein each $R_1$ is hydroxy or a straight or branched alkoxy group of from 1 to 8 carbon atoms.

3. A compound of claim 1 wherein $R_1$ is hydroxy.

4. A compound of claim 1 wherein m is 2.

* * * * *